United States Patent
Sethuraman et al.

(10) Patent No.: US 10,058,718 B2
(45) Date of Patent: Aug. 28, 2018

(54) TRANSURETHRAL ULTRASOUND PROBE FOR TREATMENT OF PROSTATE

(75) Inventors: Shriram Sethuraman, Elmsford, NY (US); Gosta Ehnholm, Helsinki (FI); Balasundara I. Raju, Tarrytown, NY (US)

(73) Assignee: Koninklijke Philips N.V., Eindhoven (NL)

( * ) Notice: Subject to any disclaimer, the term of this patent is extended or adjusted under 35 U.S.C. 154(b) by 253 days.

(21) Appl. No.: 13/202,602

(22) PCT Filed: Feb. 5, 2010

(86) PCT No.: PCT/IB2010/050538
§ 371 (c)(1),
(2), (4) Date: Aug. 22, 2011

(87) PCT Pub. No.: WO2010/100573
PCT Pub. Date: Sep. 10, 2010

(65) Prior Publication Data
US 2011/0301508 A1    Dec. 8, 2011

Related U.S. Application Data

(60) Provisional application No. 61/156,577, filed on Mar. 2, 2009.

(51) Int. Cl.
| A61H 1/00 | (2006.01) |
| A61N 7/02 | (2006.01) |
| A61B 17/00 | (2006.01) |
| A61B 18/00 | (2006.01) |
| A61B 90/00 | (2016.01) |

(52) U.S. Cl.
CPC .... *A61N 7/022* (2013.01); *A61B 2017/00911* (2013.01); *A61B 2018/00023* (2013.01); *A61B 2090/0472* (2016.02); *A61B 2090/374* (2016.02)

(58) Field of Classification Search
CPC .............................. A61N 7/00; A61H 23/0245
USPC ............................................................. 601/2
See application file for complete search history.

(56) References Cited

U.S. PATENT DOCUMENTS

| 4,936,307 A | 6/1990 | Saito et al. |
| 4,977,898 A | 12/1990 | Schwarzschild et al. |
| 5,195,519 A | 3/1993 | Angelsen |
| 5,299,578 A | 4/1994 | Rotteveel et al. |
| 5,316,000 A | 5/1994 | Chapelon et al. |
| 5,391,197 A | 2/1995 | Burdette et al. |

(Continued)

FOREIGN PATENT DOCUMENTS

| DE | 10029739 A1 | 2/2002 |
| DE | 10029739 | 7/2002 |

(Continued)

*Primary Examiner* — Hien Nguyen (57) ABSTRACT

A probe including a shaft on which an ultrasound element is mounted, an outer sheath and an acoustic membrane surrounding the shaft and the ultrasound element such that the shaft and ultrasound element are rotatable therein. Passages may supply a cooling and acoustic coupling fluid to an inlet and outlet adjacent the acoustic element to cool the acoustic element and fill a volume between the acoustic element and the acoustic sheath with the fluid. A balloon may be mounted on the probe to be selectively inflated to fix a position of the probe. A drain for urine and other bodily fluids may be provided through the probe.

23 Claims, 8 Drawing Sheets

(56) References Cited

U.S. PATENT DOCUMENTS

| | | | |
|---|---|---|---|
| 5,720,287 A * | 2/1998 | Chapelon et al. | 600/439 |
| 5,733,315 A | 3/1998 | Burdette et al. | |
| 6,379,320 B1 * | 4/2002 | Lafon et al. | 601/3 |
| 6,589,174 B1 * | 7/2003 | Chopra et al. | 600/439 |
| 7,591,794 B2 | 9/2009 | Lacoste | |
| 2002/0082610 A1 * | 6/2002 | Cioanta | A61B 18/04 606/108 |
| 2002/0111386 A1 * | 8/2002 | Sekins et al. | 514/759 |
| 2005/0131399 A1 * | 6/2005 | Loeb | A61B 18/24 606/15 |
| 2007/0010805 A1 | 1/2007 | Fedewa et al. | |
| 2008/0039746 A1 * | 2/2008 | Hissong | A61B 19/5244 601/3 |

FOREIGN PATENT DOCUMENTS

| | | |
|---|---|---|
| JP | 10192289 A | 7/1998 |
| JP | 2002017742 A | 1/2002 |
| JP | 2002516586 A | 6/2002 |
| JP | 2004216159 A | 6/2004 |
| JP | 2005185072 A | 7/2005 |
| WO | WO199215253 | 9/1992 |
| WO | 1998058588 A1 | 12/1998 |
| WO | WO200232506 | 4/2002 |

\* cited by examiner

TRANSURETHRAL ULTRASOUND PROBE FOR TREATMENT OF PROSTATE

The present application relates to ultrasound therapy probes. It finds particular application in transurethral prostate therapy, particularly thermal ablation of prostate diseases, but will also find application in other treatments to other parts of the anatomy.

Prostate cancer is estimated to be the second most frequently diagnosed cancer in American men in 2007. It is also estimated that 14 million men in the US show symptoms of another prostate disease called benign prostatic hyperplasia. The high incidences of both prostate cancer and BPH have prompted increased investigation into the treatment of these diseases. Currently accepted treatments include radical prostatectomy, external beam radiation therapy, brachytherapy, cryotherapy, hormonal therapy and chemotherapy. The above-mentioned therapies have their associated side-effects either due to being invasive, non-specific treatment, use of ionizing radiation, or the inability to identify and target localized cancer. Other non-invasive options through thermal treatment using lasers, microwaves and radio-frequency waves are becoming increasing available.

Ultrasound is quickly becoming a desired approach for specific therapeutic interventions. In particular, the use of high intensity focused ultrasound is currently being used as an approach for thermal therapeutic intervention for uterine fibroids and has been examined for possible uses in the treatment of liver, brain, prostate, and other cancerous lesions. Ultrasound therapy for tissue ablation works by insonifying a tissue of interest with high intensity ultrasound that is absorbed and converted into heat, raising the temperature of the tissues. As the temperature rises above 55° C., coagulative necrosis of the tissues occurs resulting in immediate cell death. The transducers used in therapy can be outside the body or be inserted into the body e.g. through blood vessels, urethra, rectum etc. Also, although the invention describes tissue ablation, other types of ultrasound based bio-effects can also be treated using the methods described in this application, including hemostasis, drug or gene delivery, clot dissolution etc.

Current approaches to ultrasound ablation of the prostate include transrectal devices that have been approved in Europe and several countries around the world. The limitations of these devices include long treatment time (longer than 3 to 4 hours), inability to treat large prostates (ones having anterior-posterior distance larger than 2.5-4 cm depending on the manufacturer), and impotence rates as high as 60% (although still lower than alternative techniques that report 90%). The overall prostate volume treated with these devices needs to be less than 40 cc, and in many cases, prior reduction of the size is done through the use of hormonal therapies or TURP (transurethral resection of the prostate). Other limitations are that the therapeutic ultrasound is distorted by the rectal wall before reaching the prostate and the possibility of near-field heating of the rectal wall. To overcome these difficulties, researchers have proposed transurethral ultrasound applicators wherein the single element transducers are inserted into the urethra to insonify the region in front of it, and sometimes rotated to cover the full cross-section. A transurethral design is advantageous since it provides direct acoustic access to the prostate gland without the effects of intervening tissues. In practice, several transducer elements are placed along the urethral axis in order to cover a 3D volume. The entire treatment process can be performed with the aid of image guidance using MRI, ultrasound or other techniques.

Related devices for prostate therapy have been proposed and discussed in the literature. For example, U.S. Pat. No. 5,733,315 by Burdette et al. describes a transurethral ultrasound probe containing omnidirectional ultrasonic radiators in a thin walled tube. The device has the advantage of smaller size (2.5 mm OD); however, the device is not focusable and not designed to be used under MRI guidance. Another transurethral ultrasound probe contains an MR compatible urethral applicator for the treatment of prostate diseases. The device is rotated in the urethra to target various regions of the prostate and includes circulating cooling fluid. However, the brass housing and the thin film acoustic window of the probe can cause significant damage to the urethra and surrounding tissue when rotated.

The present application provides a new and improved transurethral ultrasound probe for thermal ablation during MR imaging which overcomes the above-referenced problems and others.

In accordance with one aspect, a probe is provided for delivering therapeutic ultrasound to target locations. The probe includes an axially rotatable ultrasonic element which is supported and rotates congruently with a shaft. An acoustic membrane is mounted to cover the ultrasound element and retain an acoustic coupling and cooling fluid therein.

In accordance with a more limited aspect, a stationary outer sheath mounted with the acoustic membrane and configured to receive the ultrasound element and the shaft and to allow free rotation of the ultrasound element and shaft therein. In this manner, the ultrasound element and the shaft rotate within the outer shaft and acoustic membrane.

In accordance with another aspect, a method of using the probe includes inserting the probe through a tubular conduit and rotating the ultrasound element relative to the acoustic membrane (66) to focus the acoustic element on target locations.

In accordance with another aspect, a method of operating a therapeutic probe includes positioning the probe in a tubular passage such that an acoustically transparent membrane allows acoustic access to a target along an entire circumference of the tubular passage. A rotational position of the probe is fixed. An ultrasound element within the probe is rotated and translated and the target is irradiated with the ultrasound element through the acoustic membrane along the circumference of the tubular passage.

In accordance with a more limited aspect, the tubular passages includes the urethra and the target includes the prostate gland.

One advantage is that transurethral ultrasound probe reduces side effects.

Another advantage is that transurethral ultrasound probe can provide therapy to the entire prostate without physical trauma to the surrounding urethra.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
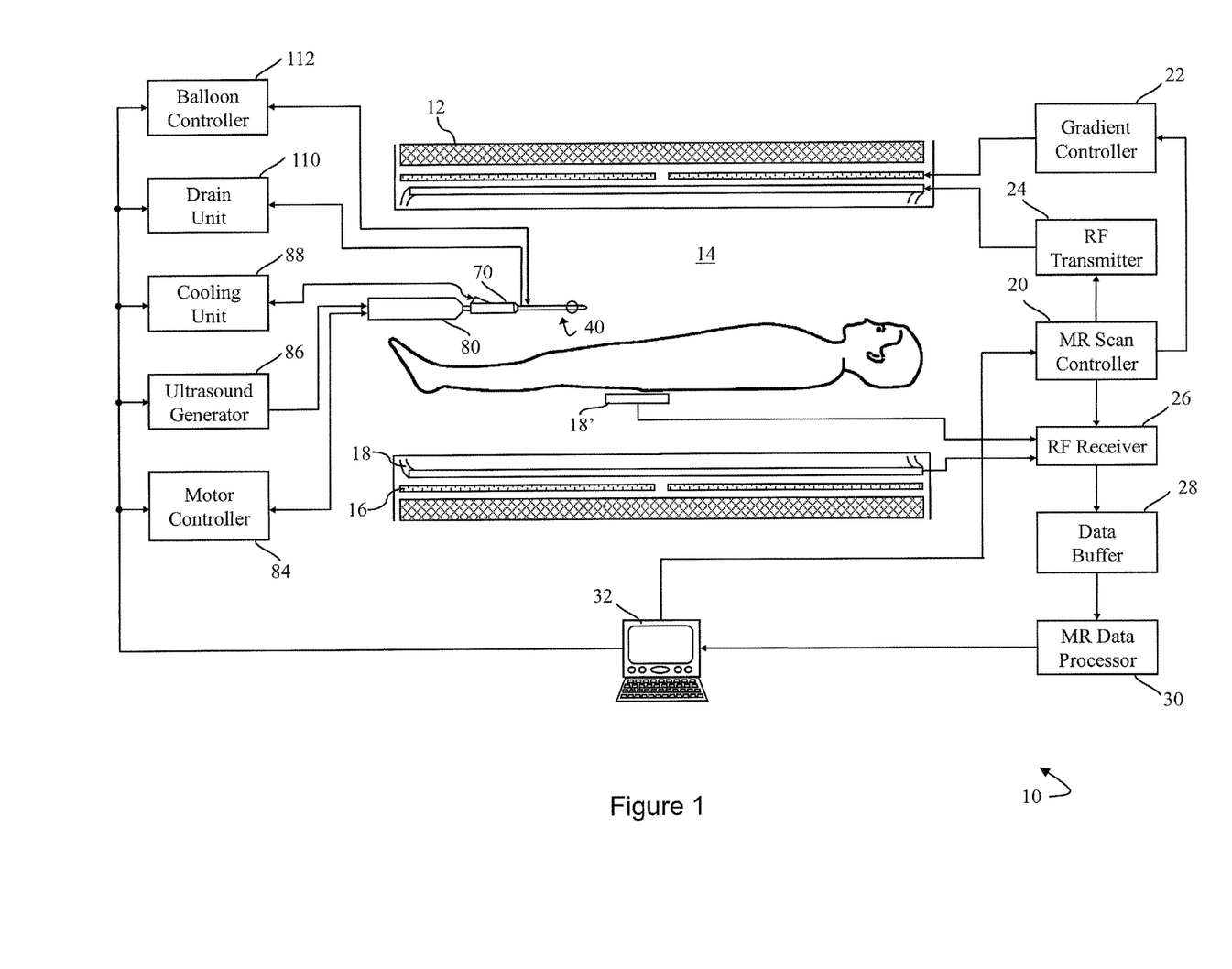
FIG. 1 is a diagrammatic side view in partial section of an MR apparatus along with a transurethral ultrasound probe.

With reference to FIG. 1, a magnetic resonance imaging system 10 includes a main magnet 12 which generates a temporally uniform $B_0$ field through an examination region 14. The main magnet can be an annular or bore-type magnet, a C-shaped open magnet, other designs of open magnets, or the like. Gradient magnetic field coils 16 disposed adjacent the main magnet serve to generate magnetic field gradients along selected axes relative to the $B_0$ magnetic field. A radio frequency coil, such as a whole-body radio frequency coil 18 is disposed adjacent the examination region. Optionally, local, surface, or dedicated transrectal RF coils 18' are provided in addition to or instead of the whole-body RF coil 18.

A scan controller 20 controls a gradient controller 22 which causes the gradient coils to apply selected magnetic field gradient pulses across the imaging region, as may be appropriate to a selected magnetic resonance imaging or spectroscopy sequence. The scan controller 20 also controls an RF transmitter 24 which causes the whole-body or local RF coils to generate magnetic resonance excitation and manipulation $B_1$ pulses. The scan controller also controls an RF receiver 26 which is connected to the whole-body or local RF coils to receive magnetic resonance signals therefrom.

The received data from the receiver 26 is temporarily stored in a data buffer 28 and processed by a magnetic resonance data processor 30. The magnetic resonance data processor can perform various functions as are known in the art, including image reconstruction, magnetic resonance spectroscopy, catheter or interventional instrument localization, and the like. Reconstructed magnetic resonance images, spectroscopy readouts, interventional instrument location information, and other processed MR data are displayed on a graphic user interface 32. The graphic user interface 30 also includes a user input device which a clinician can use for controlling the scan controller 20 to select scanning sequences and protocols, and the like.

A transurethral probe 40 for delivering therapeutic ultrasound to prostate tissues is operated by the surgeon or clinician. The probe is localized using real-time MRI imaging. Continuing with reference to FIGS. 2, 7A, and 7B, therapeutic ultrasound energy is directed toward the prostate by energizing an ultrasound array 42 at the distal end of the probe 40. The ultrasound array may contain a single or a plurality of ultrasound transducers elements stacked on a transducer housing 44. The ultrasound transducers elements are constructed from MR compatible materials such as PZT, Ferroperm PZ-52™, or other non-magnetic materials suitable for ultrasound transducers. A non-magnetic matching layer is disposed on the active face of the transducer elements such as an aluminum oxide doped epoxy layer. In addition to the ultrasound array, the transducer housing includes at least two channels with an inlet and outlet 48 for circulating cooling and coupling fluid 46 across the active face of the ultrasound array. The channel inlet and outlet 48 are disposed on either side of the ultrasound array and make sure that the fluid is circulated across the transducer array as well as throughout the probe to prevent the transducers from overheating. Further, the cooling tubes help maintain the temperature of the urethral wall and surrounding tissues below the damage threshold. Additionally, the fluid provides an acoustic coupling between the transducer array and the adjacent tissue. In addition to the cooling tubes, the transducer housing also contains electrode leads 50 for energizing the ultrasound elements. The small coolant tubes and the electrode leads are individually enclosed in small plastic tubes and disposed in a pool of epoxy. The transducer housing may be constructed out of a plastic resin such as Ultem™ (thermoplastic polyetherimide) or the like.

Figure 2:
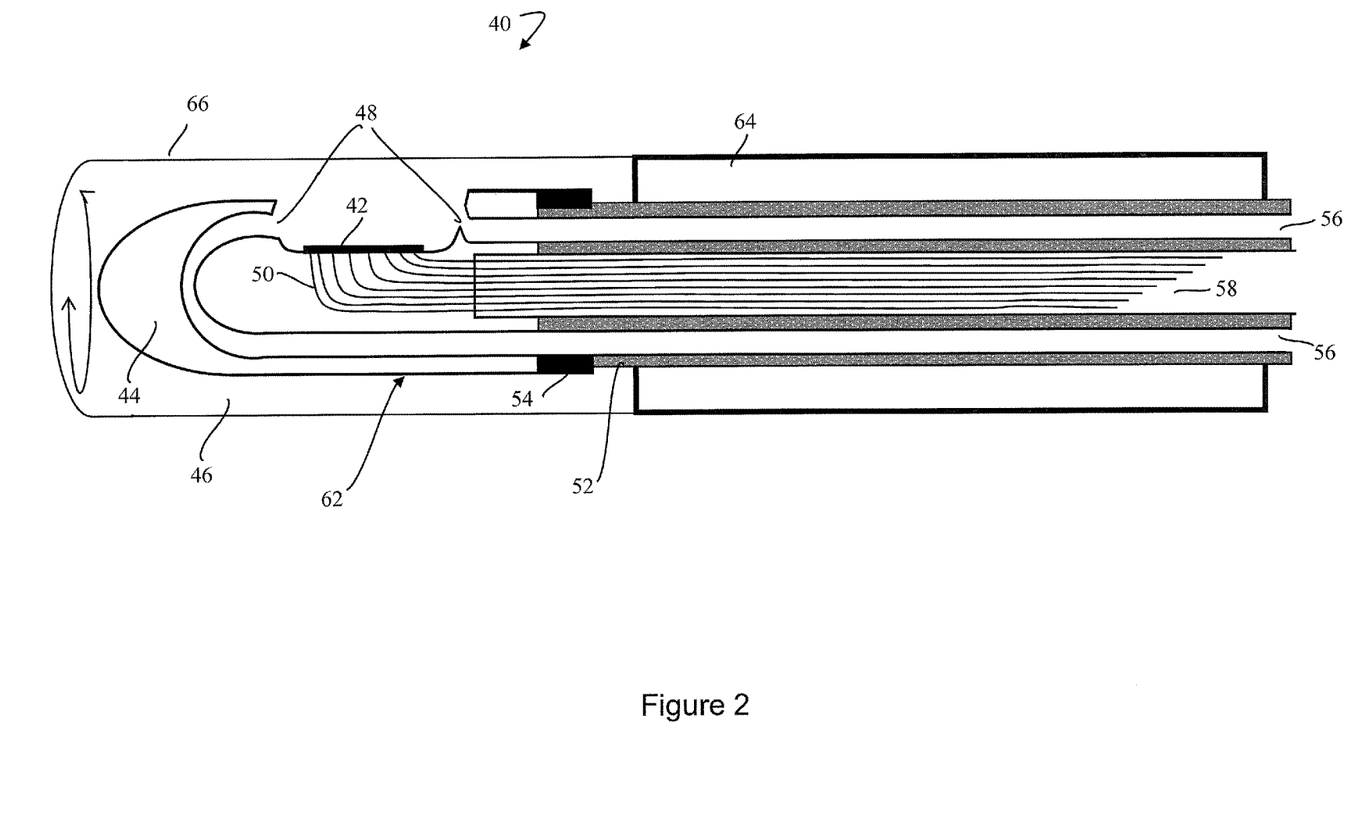
FIG. 2 is a diagrammatic side view in partial section of the distal end of a transurethral ultrasound probe.

The transducer housing is affixed to a stiff shaft 52, e.g. with epoxy 54, to form a single rigid member. The cooling channels 56 and electrode leads 58 are bundled together and further enclosed in epoxy within the shaft. The shaft can be constructed from fiberglass, carbon fiber composites, or the like. The transducer housing and the shaft together make up a transurethral ultrasound device 62.

The ultrasound device is further enclosed in an outer sheath 64. The sheath is a thick-walled single lumen tube constructed from plastic or other MR compatible material that provides structural integrity to the ultrasound device. The ultrasound device is positioned in the sheath such that the ultrasound array lies outside the distal end of the sheath. During therapy, the ultrasound device is free to rotate in the sheath permitting complete circumferential ultrasound transmission along the axial direction which allows access to all parts of the prostate.

A tubular acoustic membrane 66 is mounted to the sheath 64 that wraps around the ultrasound array and allows 360 degree acoustic access to the prostate and surrounding tissue. The membrane defines a volume that stores the cooling and coupling fluid and provides structure and rigidity at the tip of the device to facilitate urethral insertion. The membrane should be less than one acoustic wavelength to maximize transmission efficiency and constructed from a material that permits maximum acoustic energy transmission to the surrounding tissue. Possible materials include, but not limited to, TPX (polymethlypentene), PET (polyethylene terephthalate), and polyamide.

Figure 3:
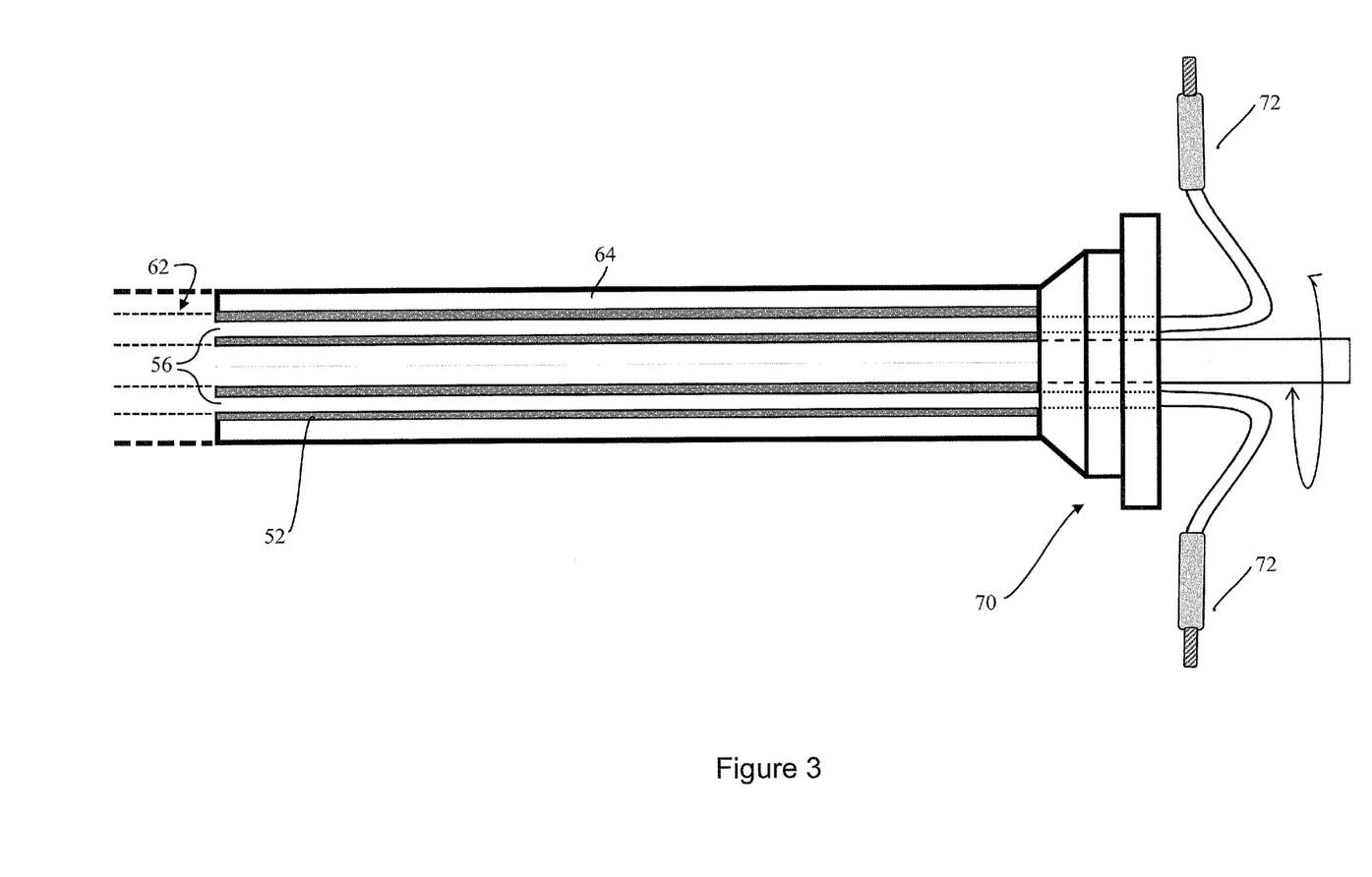
FIG. 3 is a diagrammatic side view in partial section of the proximal end of a transurethral ultrasound probe.
Figure 7A:
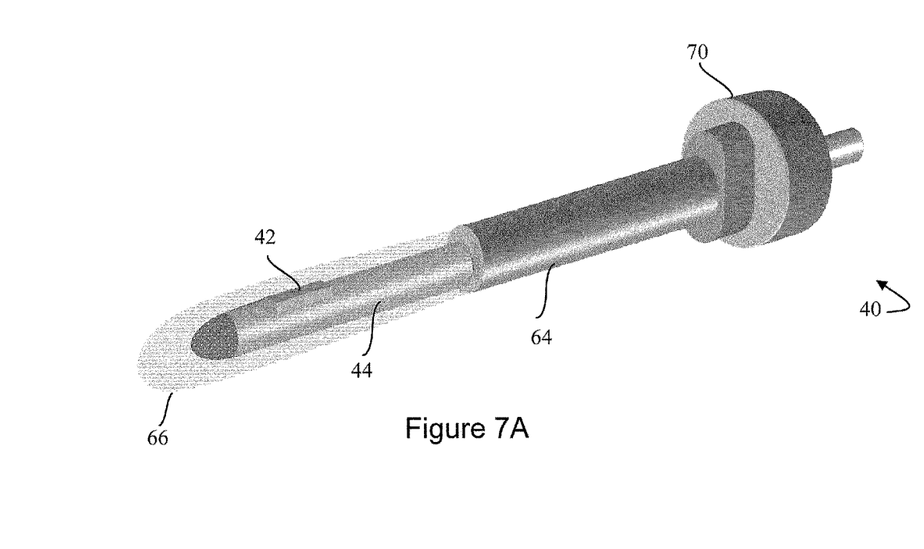
FIGS. 7A through 7C are three-dimensional renderings of a transurethral ultrasound probe.
Figure 7B:
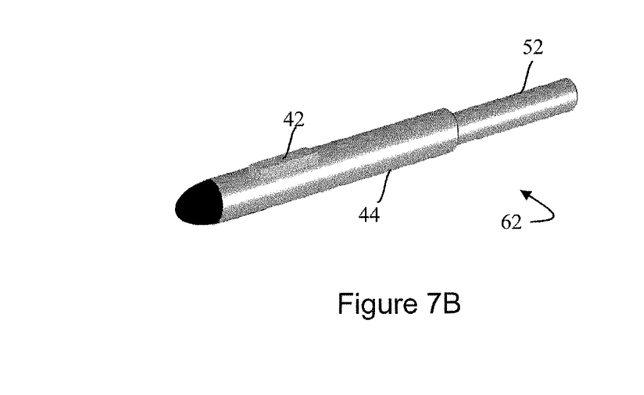
Figure 7C:
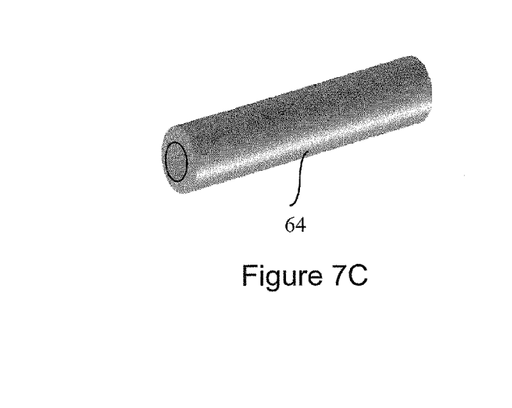
Figure 8:
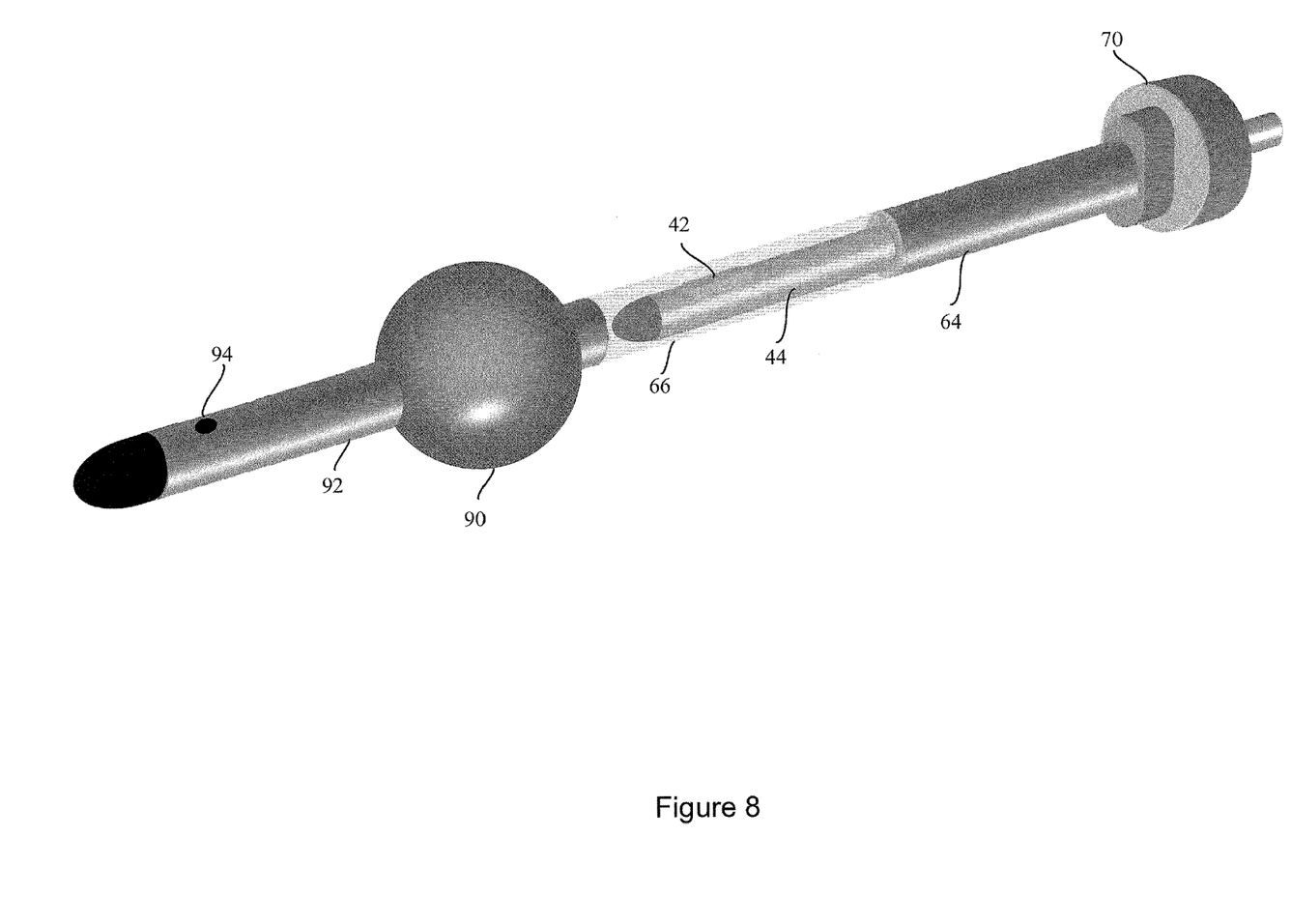
FIG. 8 is a three-dimensional rendering of the transurethral ultrasound probe along with a positioning balloon and urinary drainage system.

With reference to FIGS. 3, 7A and 7C, the proximal end of the probe terminates into a plug housing 70. The plug housing is attached to the outer sheath 64 so that the outer portion of the probe (the sheath 64 and acoustic membrane 66) can be held mechanically avoiding movement during rotation of the enclosed ultrasound device 62. The fluid conduits 56 terminate into luer adapters 72 made from plastic or similar material.

Figure 9:
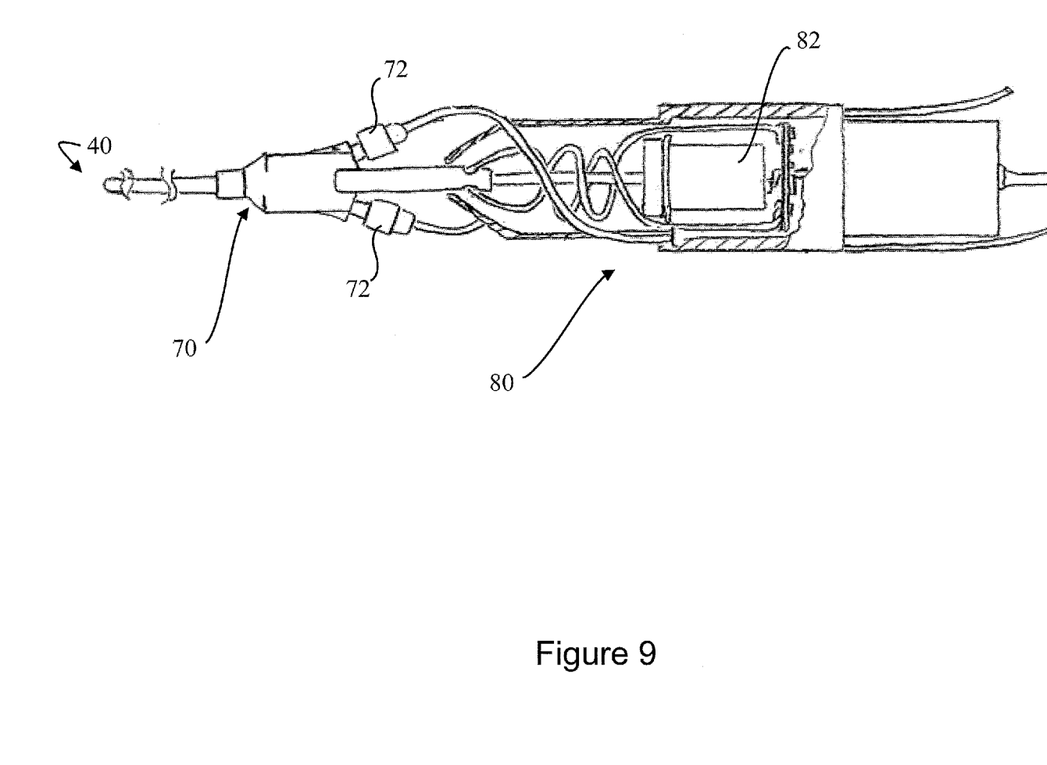
FIG. 9 is a diagrammatic side view in partial section of the plug housing and rotator housing of a transurethral ultrasound probe.

With continuing reference to FIG. 1, the plug housing 70 can be attached to a rotator housing 80 which includes mechanical means for rotating the ultrasound device 62. Optionally, the ultrasound device can be rotated manually by an operator. Within the rotator housing is at least one MRI compatible non-magnetic piezomotor 82 to rotate and/or linearly translate the ultrasound device as illustrated in FIG. 9. It should be appreciated that a hydraulic motor or a compressed air driven pneumatic motor is also contemplated for rotation and/or translation of the ultrasound device. The piezomotor is connected to a motor controller 84 (FIG. 1) that is capable of sending and receiving data related to the rotational position of the ultrasound array and changing the rotational position of the ultrasound array.

The electrical leads 58 from the ultrasound array continue through the shaft 52, plug housing 70, and rotator housing 80 to an ultrasound generator 86. The ultrasound generator is made up of RF power amplifiers, an RF power monitoring system, and a multi-channel signal synthesizer. The synthesizer is capable of controlling the output ultrasound waveform and controlling the focal point depth and lateral position of the ultrasound beam.

The luer connectors 72 at the terminal end of the fluid conduits 56 attach to a cooling unit 88. The cooling unit is made up of a refrigeration unit for cooling the fluid and maintaining the cooled temperature; additionally, the cooling unit includes a recirculation pump configured to recirculate the fluid and optionally is capable of removing bubbles formed during the ultrasound therapy. A suitable cooling and coupling fluid is degassed water, but other fluids are contemplated.

In an alternative embodiment, the transducer housing 44 could be constructed of brass, an MRI compatible material with improved thermal conductivity. The brass transducer housing could enhance conduction of heat away from the transducer elements. In addition to improved thermal conductivity, the brass transducer housing can provide additional rigidity to the tip of the probe to facilitate insertion into the urethra. The brass housing may also serve has a common electrical ground thus reducing the number of electrical leads and the overall size of the ultrasound device.

In an alternative embodiment, the ultrasound array is composed of a single ultrasound transducer element. The ultrasound device 62 is linearly translated and rotated within the probe 40, either manually or mechanically by piezomotors, to cover the lateral and rotational extent of the prostate during therapy. A single transducer element will allow targeting narrow regions of the prostate and perform focal therapy. The reduction in the number of transducer elements will further reduce the size of the therapeutic device by reducing the size of the transducer housing, the number of electrical leads, and volume of cooling fluid required to maintain a stable operating temperature.

Figure 4:
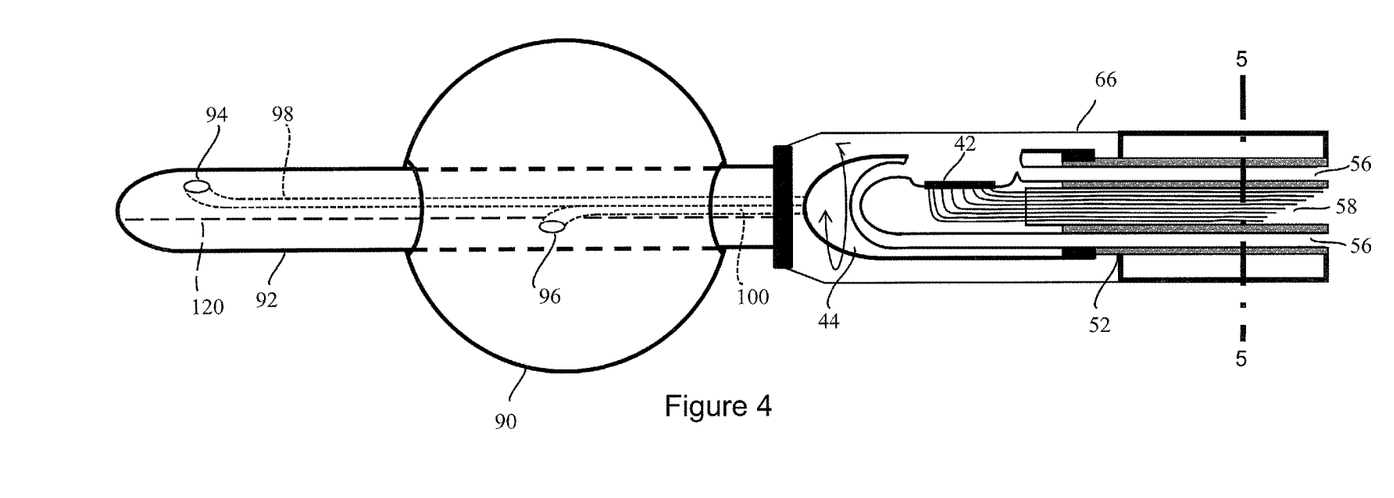
FIG. 4 is a diagrammatic side view in partial section of the distal end of a transurethral ultrasound probe along with a positioning balloon and urinary drainage system.
Figure 5:
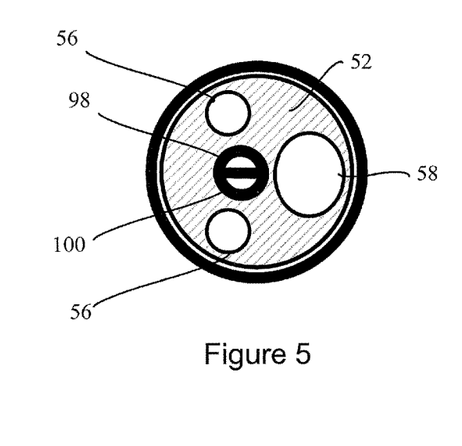
FIG. 5 is a diagrammatic cross-section view of a transurethral ultrasound probe along with a positioning balloon and urinary drainage system.
Figure 6:
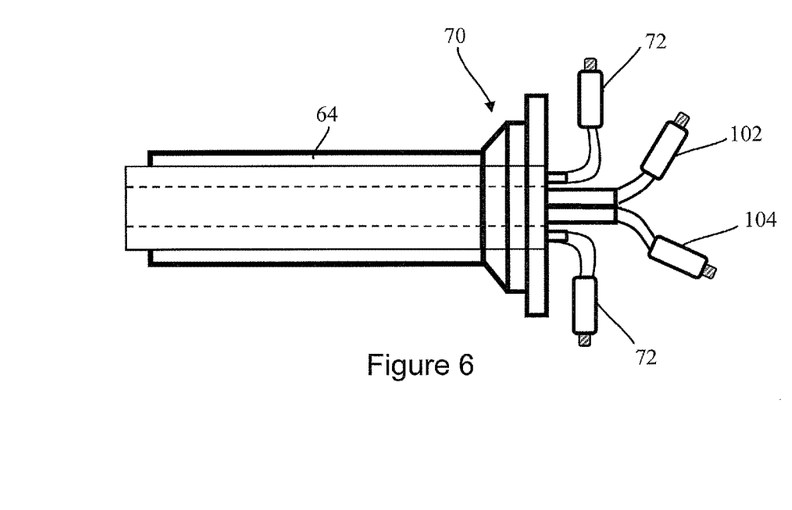
FIG. 6 is a diagrammatic side view in partial section of the proximal end of a transurethral ultrasound probe along with a positioning balloon and urinary drainage system.

With reference to FIGS. 4A and 4B, in one embodiment a positioning balloon 90 and a drainage system 92 are included adjacent the distal tip of the probe. Although illustrated closer to the distal end than the ultrasound array, it is to be appreciated that the ultrasonic array could be closer to the distal end. With appropriate acoustic materials, the balloon could surround the ultrasonic array. The positioning balloon is inflated, e.g. in the bladder, to fix the translational position of the probe in place. Optionally, the positioning balloon can fix the rotational position of the probe. Included with the positioning balloon, a catheter with a drain eye or aperture 94 to drain the urine from the bladder or other fluids that make up the drainage system. The catheter travels through the positioning balloon and includes an inflation eye 96 for supplying fluid to inflate the balloon. The drain eye and inflation eye are connected to a fluid drain conduit 98 and an inflation fluid conduit 100 respectively that are housed within the catheter. The fluid and gas conduits continue through the probe into the shaft 52 as shown in FIG. 5, a cross section of the probe at line 5-5. At the proximal end of the probe, shown in FIG. 6, the additional fluid conduits terminate into luer adapters 102 and 104. With continuing reference to FIG. 1, luer adapter 102 is connected to a drain unit 110 which collects the urine drained from the bladder. Luer adapter 104 is connected to a balloon controller 112 which is responsible for inflating the balloon when positioned in the bladder. In one embodiment, the balloon controller inflates the balloon with an MR tracer or MR imageable substance in order to facilitate using MR to locate the catheter.

In another embodiment, the probe is flexible. A guide wire 120 extends through the probe to the distal end to curve or bend the distal end to facilitate passing the probe through curved passages. Although described with reference to treating the prostate, it will be appreciated that the probe is suitable for other applications, including but not limited to vaginal, arterial, tracheal, and rectal focused ultrasound therapy.

In another embodiment, the rotator housing includes a plurality of piezomotors for linearly translating the ultrasound device and for independent rotation of both the outer portion of the probe (sheath 64 and acoustic membrane 66) and the enclosed ultrasound device 62 in the same and/or opposite directions.

In another embodiment, the sheath 64 is composed of a flexible material. The flexible material permits the outer portion of the probe (sheath 64 and acoustic membrane 66) to be rotated congruently with the enclosed ultrasound device 62. The flexible sheath will reduce risk of trauma on the surrounding urethra because the normal force exerted on the urethra by the flexible sheath is less than the normal force exerted by a stiff shaft, thus reducing friction. Additionally, the embodiment may include a positioning balloon 90 and fluid drainage system 92 which rotate congruently with the entire probe.

Figure 10A:
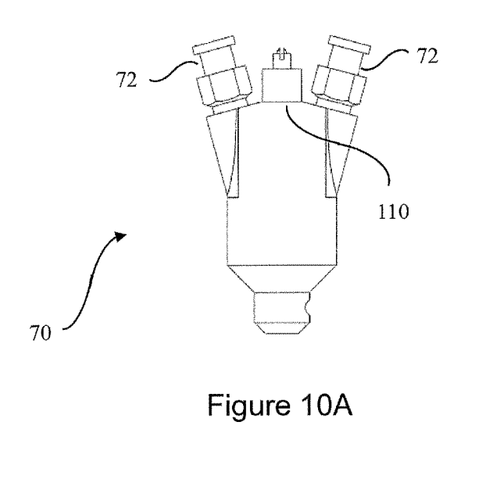
FIGS. 10A through 10D are three-dimensional schematic drawings of the plug housing and electric plug connector.
Figure 10B:
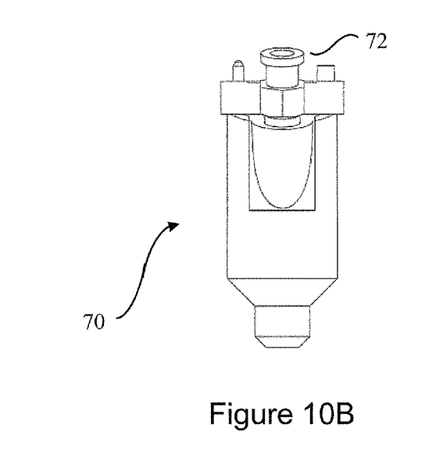
Figure 10C:
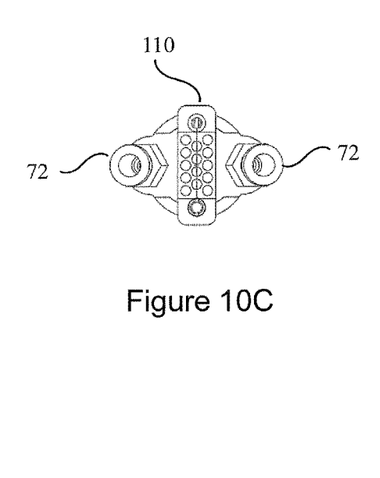
Figure 10D:
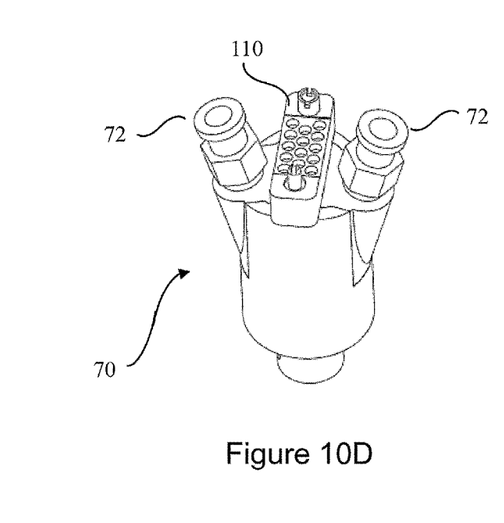

In another embodiment, the plug housing 70 can be detachable connected to the rotator housing 80. The attachment and/or detachment means can be an electric plug connector 110 (FIG. 10A-10C). In this manner, the probe can be positioned in the urethra without the rotator housing. Once the probe is positioned relative to the prostate, the rotator housing can be connected to the probe via the plug housing and therapy can commence. This arrangement can reduce the time required by the surgeon of clinician to position the probe by minimizing the number of components coupled to the probe. The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. An MR compatible probe for delivering therapeutic ultrasound to target locations, the probe comprising:
    an axially rotatable ultrasound element;
    electrode leads coupled to the ultrasound element;
    a shaft adjacent the ultrasound element configured to support and rotate congruently with the ultrasound element;
    fluid conduits enclosed within the shaft to circulate a cooling and acoustic coupling fluid;
    an acoustic membrane mounted to cover the ultrasound element and retain the acoustic coupling and cooling fluid therein, wherein the acoustic membrane is a tubular membrane that surrounds the ultrasound element and is configured for omni-directional acoustic transparency circumferentially as the ultrasonic element is rotated therein and the ultrasound element is configured to irradiate the target locations along a circumference of the acoustic membrane;

at least one inlet and outlet pair connected with the fluid conduits thereby forming inlet and outlet fluid conduits that each extend along and directly adjacent to both an inside periphery of an outermost wall of the probe out through a proximate tip of the shaft and an outside periphery of the electrode leads thereby being configured to provide a fluid path to circulate the cooling and acoustic coupling fluid over an active face of the ultrasound element;

a transducer housing which supports a non-active face of the ultrasound element to the shaft to form a rigid member, the transducer housing having a depression inside which the non-active face of the ultrasound element is supported;

an aperture and a conduit leading from the aperture through the probe to convey fluids, wherein the aperture is positioned adjacent a distal end of the probe and the conduit is separate from the inlet and outlet fluid conduit; and a stationary outer sheath mounted with the acoustic membrane and configured to receive the ultrasound element and the shaft and allow free rotation of the ultrasound element, and the shaft therein such that the ultrasound element, the shaft, the at least one inlet and outlet pair and the inlet and outlet fluid conduits rotate within the outer sheath and the acoustic membrane while the outer sheath and the acoustic membrane remain stationary, wherein the at least one inlet and outlet pair are defined on opposite sides of the active face of the ultrasound element and are configured to maintain the positioning on the opposite sides of the active face at all axial positions of the axially rotatable ultrasound element.

2. The probe according to claim 1, wherein the electrode leads are positioned between the inlet and outlet fluid conduits.

3. The probe according to claim 1, wherein a bottom of the depression is sized larger than the non-active face of the ultrasound element and extends in a same plane as the non-active face of the ultrasound element.

4. The probe according to claim 1, wherein
a wall thickness of the acoustic membrane is less than one acoustic wavelength emitted by the ultrasound element; and
the acoustic membrane defines an enclosed volume configured to be filled with the cooling and coupling fluid.

5. The probe according to claim 1; further including:
a balloon disposed closer to the distal end of the probe then the ultrasound element so as to avoid the irradiating of the target locations along the circumference of the acoustic membrane; and
a fluid conduit which supplies fluid to the balloon to inflate the balloon.

6. The probe according to claim 1, wherein the aperture is disposed closer to the distal end of the probe then the ultrasound element.

7. The probe according to claim 1, further including:
a rotator mounting configured with at least one non-magnetic piezomotor to rotate and/or translate the ultrasound element and the shaft; and
a plug housing at a proximal end of the probe configured to mechanically hold the outer sheath to avoid movement during rotation of the rigid member,
wherein the rotator mounting and plug housing are detachably connected via an electric plug connector.

8. The probe according to claim 1, further including:
a plug housing at a proximal end of the probe configured to mechanically hold the outer sheath to avoid movement during rotation of the rigid member,
wherein the plug housing is detachably connected via an electric plug connector to allow the probe to be position prior to attaching the rotator mounting.

9. The probe according to claim to claim 1, wherein the sheath and shaft are composed of flexible materials.

10. A magnetic resonance imaging system, comprising:
a magnet which generates a static magnetic field in an examination region;
a radiofrequency transmit coil configured to induce and manipulate magnetic resonance in a subject in the examination region and/or acquire magnetic resonance data from the examination region;
an axially rotatable ultrasound element;
electrode leads coupled to the ultrasound element;
a shaft adjacent the ultrasound element configured to support and rotate congruently with the ultrasound element;
fluid conduits enclosed within the shaft to circulate a cooling and acoustic coupling fluid;
an acoustic membrane mounted to cover the ultrasound element and retain the acoustic coupling and cooling fluid therein, wherein the acoustic membrane is a tubular membrane that surrounds the ultrasound element and is configured for omni-directional acoustic transparency circumferentially as the ultrasonic element is rotated therein and the ultrasound element is configured to irradiate the target locations along a circumference of the acoustic membrane;
at least one inlet and outlet pair connected with the fluid conduits thereby forming inlet and outlet fluid conduits that each extend along and directly adjacent to both an inside periphery of an outermost wall of the shaft out through a proximate tip of the shaft and an outside periphery of the electrode leads thereby being configured to provide a fluidic path to circulate the cooling and acoustic coupling fluid over an active face of the ultrasound element;
a transducer housing which supports a non-active face of the ultrasound element to the shaft to form a rigid member, the transducer housing having a depression inside which the non-active face of the ultrasound element is supported;
an aperture and a conduit leading from the aperture through the probe to convey fluids, wherein the aperture is positioned adjacent a distal end of the probe and the conduit is separate from the inlet and outlet fluid conduit; and
a stationary outer sheath mounted with the acoustic membrane and configured to receive the ultrasound element and the shaft and allow free rotation of the ultrasound element and the shaft therein such that the ultrasound element, the shaft, the at least one inlet and outlet pair and the inlet and outlet fluid conduits rotate within the outer sheath and the acoustic membrane while the outer sheath and the acoustic membrane remain stationary,
wherein the at least one inlet and outlet pair are defined on opposite sides of the active face of the ultrasound element and are configured to maintain the positioning on the opposite skies of the active face at all axial positions of the axially rotatable ultrasound element.

11. The magnetic resonance imaging system according to claim 10, comprising:
a balloon disposed closer to the distal end of the transducer housing then the ultrasound element so as to avoid the irradiating of the target locations along the circumference of the acoustic membrane; and a balloon controller configured to control inflation of the balloon.

12. A method of operating a therapeutic probe comprising acts of:

positioning a probe in a tubular passage such that an acoustically transparent membrane that is tubular and a stationary outer sheath mounted with the acoustic membrane to receive an ultrasound element coupled to electrode leads and a shaft adjacent the ultrasound element to support and rotate congruently with the ultrasound element and allow free rotation of the ultrasound element and the shaft therein such that the ultrasound element and the shaft are rotatable within the outer sheath and the acoustic membrane while the outer sheath and the acoustic membrane remain stationary, the acoustic membrane and the outer sheath surrounds the probe and the acoustic membrane is configured for omni-directional acoustic transparency circumferentially and thereby allows acoustic access to targets around a circumference of the tubular passage;

cooling an active face of the ultrasound element through inlet and outlet fluid conduits positioned within the shaft and connected with at least one inlet and outlet pair, the inlet and outlet fluid conduits each extending along and directly adjacent to both an inside periphery of an outermost wall of the probe out through a proximate tip of the shaft and an outside periphery of the electrode leads thereby providing a fluid path circulating the cooling and acoustic coupling fluid over an active face of the ultrasound element;

supporting a non-active face of the ultrasound element to the shaft with a transducer housing to form a rigid member, the transducer housing having a depression inside which the non-active face of the ultrasound element is supported;

positioning adjacent a distal end of the probe, an aperture and a conduit leading from the aperture through the probe to convey fluids, wherein the conduit is separate from the inlet and outlet fluid conduits;

rotating and translating an ultrasound element within the probe through rotation of the shaft within the outer heath, the at least one inlet and outlet pair, the inlet and outlet fluid conduits and the acoustic membrane while the outer sheath and the acoustic membrane remain stationary;

with the ultrasound element, irradiating the targets through the acoustic membrane along the circumference of the tubular passage, wherein the at least one inlet and outlet pair are defined on opposite sides of the active face of the ultrasound element and maintain the positioning on the opposite sides of the active face at all axial positions of the axially rotatable ultrasound element.

13. The method of claim 12, comprising acts of:
inserting the probe through a tubular conduit;
rotating the ultrasound element to focus the ultrasound element on target locations relative to the acoustic membrane.

14. The method according to claim 12, wherein the ultrasound element includes a variable focus planar array composed of non-magnetic ultrasound transducers, wherein the act of irradiating the target comprises an act of selectively activating individual transducers to perform focal therapy on intended target regions.

15. The method according to claim 12, further including an act of:
circulating the cooling and coupling fluid inside the acoustically transparent membrane through the inlet and outlet fluid conduits coupled to the at least one inlet and outlet pair defined on opposite sides of the active face of the ultrasound element.

16. The method according to claim 12, further including acts of:
positioning a balloon coupled to the probe and disposed at the distal end of the probe so as to avoid the irradiating of the target locations along the circumference of the acoustic membrane; and
inflating the balloon to lock the probe into place.

17. The method according to claim 12, further including an act of:
draining fluid through the probe through the aperture and the conduit leading from the aperture, wherein the aperture is positioned adjacent the distal end past the ultrasound element.

18. The method according to claim 12, wherein the inlet and outlet fluid conduits each extend along an inside periphery of the shaft and the act of rotating and translating the ultrasound element further including an act of:
maintaining a positioning of the at least one inlet and outlet pair connected on opposite sides of the active face of the ultrasound element and the inlet and outlet fluid conduits with respect to the ultrasound element at all axial positions of the ultrasound element.

19. The method according to claim 12, wherein the method is performed for vaginal, arterial, tracheal, prostate, or rectal focused ultrasound therapy.

20. The probe according to claim 1, wherein one of the fluid conduits forms a ridge thereby deflecting the fluid path adjacent to the ultrasound element.

21. An MR compatible probe for delivering therapeutic ultrasound to target locations, the probe comprising:
an axially rotatable ultrasound element;
electrode leads coupled to the ultrasound element;
a shaft adjacent the ultrasound element configured to support and rotate congruently with the ultrasound element;
fluid conduits enclosed within the shaft to circulate a cooling and acoustic coupling fluid;
an acoustic membrane mounted to cover the ultrasound element and retain the acoustic coupling and cooling fluid therein, wherein the acoustic membrane is a tubular membrane that surrounds the ultrasound element and is configured for omni-directional acoustic transparency circumferentially as the ultrasonic element is rotated therein and the ultrasound element is configured to irradiate the target locations along a circumference of the acoustic membrane;
at least one inlet and outlet pair defined adjacent the ultrasound element and connected with the fluid conduits thereby forming inlet and outlet fluid conduits that each extend along and directly adjacent to both an inside periphery of an outermost wall of the probe out through a proximate tip of the shaft and an outside periphery of the electrode leads thereby being configured to provide a fluid path to circulate the cooling and acoustic coupling fluid over an active face of the ultrasound element; and
a stationary outer sheath mounted with the acoustic membrane and configured to receive the ultrasound element and the shaft and allow free rotation of the ultrasound element, and the shaft therein such that the ultrasound element, the shaft, the at least one inlet and outlet pair and the inlet and outlet fluid conduits rotate within the outer sheath and the acoustic membrane while the outer sheath and the acoustic membrane remain stationary, wherein one of the fluid conduits forms a ridge in one of the inlet and outlet fluid conduits rising above the ultrasound element thereby deflecting the fluid path adjacent to the ultrasound element.

22. A magnetic resonance imaging system, comprising:

a magnet which generates a static magnetic field in an examination region;

a radiofrequency transmit coil configured to induce and manipulate magnetic resonance in a subject in the examination region and/or acquire magnetic resonance data from the examination region;

an axially rotatable ultrasound element;

electrode leads coupled to the ultrasound element;

a shaft adjacent the ultrasound element configured to support and rotate congruently with the ultrasound element;

fluid conduits enclosed within the shaft to circulate a cooling and acoustic coupling fluid;

an acoustic membrane mounted to cover the ultrasound element and retain the acoustic coupling and cooling fluid therein, wherein the acoustic membrane is a tubular membrane that surrounds the ultrasound element and is configured for omni-directional acoustic transparency circumferentially as the ultrasonic element is rotated therein and the ultrasound element is configured to irradiate the target locations along a circumference of the acoustic membrane;

at least one inlet and outlet pair defined adjacent the ultrasound element and connected with the fluid conduits thereby forming inlet and outlet fluid conduits that each extend along and directly adjacent to both an inside periphery of an outermost wall of the shaft out through a proximate tip of the shaft and an outside periphery of the electrode leads thereby being configured to provide a fluidic path to circulate the cooling and acoustic coupling fluid over an active face of the ultrasound element; and a stationary outer sheath mounted with the acoustic membrane and configured to receive the ultrasound element and the shaft and allow free rotation of the ultrasound element and the shaft therein such that the ultrasound element; the shaft, the at least one inlet and outlet pair and the inlet and outlet fluid conduits rotate within the outer sheath and the acoustic membrane while the outer sheath and the acoustic membrane remain stationary, wherein one of the fluid conduits forms a ridge in one of the inlet and outlet fluid conduits rising above the ultrasound element thereby deflecting the fluidic path adjacent to the ultrasound element.

23. A method of operating a therapeutic probe comprising acts of:

positioning a probe in a tubular passage such that an acoustically transparent membrane that is tubular and a stationary outer sheath mounted with the acoustic membrane to receive an ultrasound element coupled to electrode leads and a shaft adjacent the ultrasound element to support and rotate congruently with the ultrasound element and allow free rotation of the ultrasound element and the shaft therein such that the ultrasound element and the shaft are rotatable within the outer sheath and the acoustic membrane while the outer sheath and the acoustic membrane remain stationary, the acoustic membrane and the outer sheath surrounds the probe and the acoustic membrane is configured for omni-directional acoustic transparency circumferentially and thereby allows acoustic access to targets around a circumference of the tubular passage;

cooling an active face of the ultrasound element through inlet and outlet fluid conduits positioned within the shaft and connected with at least one inlet and outlet pair defined adjacent the ultrasound element, the inlet and outlet fluid conduits each extending along and directly adjacent to both an inside periphery of an outermost wall of the probe out through a proximate tip of the shaft and an outside periphery of the electrode leads thereby providing a fluid path circulating the cooling and acoustic coupling fluid over an active face of the ultrasound element;

rotating and translating an ultrasound element within the probe through rotation of the shaft within the outer sheath, the at least one inlet and outlet pair, the inlet and outlet fluid conduits and the acoustic membrane while the outer sheath and the acoustic membrane remain stationary;

with the ultrasound element, irradiating the targets through the acoustic membrane along the circumference of the tubular passage, wherein one of the inlet and outlet fluid conduits forms a ridge in one of the inlet and outlet fluid conduits rising above the ultrasound element thereby deflecting the fluid path adjacent to the ultrasound element.

* * * * *